US008445252B2

(12) United States Patent
Nakasaki et al.

(10) Patent No.: US 8,445,252 B2
(45) Date of Patent: May 21, 2013

(54) METHOD FOR PRODUCING FUNCTIONAL COMPOST, FUNCTIONAL COMPOST AND COMPOST FOR PROLIFERATION OF FILAMENTOUS FUNGUS

(75) Inventors: Kiyohiko Nakasaki, Yokohama (JP); Nobuaki Suzuki, Yokohama (JP)

(73) Assignee: National University Corporation Shizuoka University, Shizuoka-shi (JP)

( * ) Notice: Subject to any disclaimer, the term of this patent is extended or adjusted under 35 U.S.C. 154(b) by 415 days.

(21) Appl. No.: 12/602,463

(22) PCT Filed: Jun. 2, 2008

(86) PCT No.: PCT/JP2008/060169
§ 371 (c)(1),
(2), (4) Date: Mar. 1, 2010

(87) PCT Pub. No.: WO2008/149846
PCT Pub. Date: Dec. 11, 2008

(65) Prior Publication Data
US 2010/0212384 A1    Aug. 26, 2010

(30) Foreign Application Priority Data
May 31, 2007  (JP) ................................. 2007-145697

(51) Int. Cl.
*C12P 1/00* (2006.01)
*C12N 1/00* (2006.01)

(52) U.S. Cl.
USPC .................... 435/243; 435/254.1; 435/252.5; 435/170; 435/171; 435/41

(58) Field of Classification Search
USPC .............. 424/93.1, 93.4, 93.5; 435/170, 171, 435/243, 254.1, 252.5
See application file for complete search history.

(56) References Cited

U.S. PATENT DOCUMENTS

| | | | |
|---|---|---|---|
| 6,524,998 B1 * | 2/2003 | Kloepper et al. | ............. 504/100 |
| 2008/0248058 A1 | 10/2008 | Nakasaki et al. | |

FOREIGN PATENT DOCUMENTS

| | | | |
|---|---|---|---|
| JP | 6-319529 | A | 11/1994 |
| JP | 9-20891 | | 1/1997 |
| JP | 10-150978 | A | 6/1998 |
| JP | 11-187866 | A | 7/1999 |
| JP | 2002 003 291 | * | 1/2002 |
| JP | 2002-204685 | A | 7/2002 |
| JP | 2003-95775 | | 4/2003 |
| JP | 2003-334061 | A | 11/2003 |
| JP | 2004-352602 | A | 12/2004 |
| JP | 2006 131 487 | * | 5/2006 |
| WO | WO-97/31521 | A1 | 9/1997 |
| WO | WO-2006/085567 | A1 | 8/2006 |

OTHER PUBLICATIONS

Re 36,232, Jun. 1999.*
An et al., "*Virgibacillus halophilus* sp. nov., Spore-forming Bacteria Isolated from Soil in Japan," *International Journal of Systematic and Evolutionary Microbiology*, 57:1607-1611 (2007).
Nakasaki et al., "Biological Control of Plant Disease Using Funcational Compost," 59th Annual Meeting of the Society for Biotechnology (2007). Translation.
Nakasaki et al., "Production of Functional Compost Containing High Concentration of Filamentous Fungus Which Can Control Plant Diseases," 39th Autumn Meeting of the Society of Chemical Engineers, pp. 1-3 (2007). Translation.
Nakasaki et al., "Production of Functional Compost Having Plant Disease Control Effect," Collected Papers of the 18th Annual Conference of the Japan Society of Waste Management Experts, pp. 1-6 (2007). Translation.
Nakasaki et al., "Production of Functional Compost Using Novel Filamentous Fungus Having Phytopathogenic Fungus Suppression Effect," 72nd Annual Meeting of the Society of Chemical Engineers, pp. 1-3 (2007). Translation.

* cited by examiner

*Primary Examiner* — Ruth Davis
(74) *Attorney, Agent, or Firm* — Marshall, Gerstein & Borun LLP

(57) ABSTRACT

The method for producing functional compost according to the invention includes: inoculating a filamentous fungus with a function, such as the *Coprinus curtus* GM-21 strain (NITE BP-37) with a plant disease control function, into compost in an bacterial-activity-restricted state which is, for example, at least one state selected from the group consisting of a nutrient-restricted state, a pH-restricted state and a water content-restricted state; and cultivating the filamentous fungus in the compost to allow its selective proliferation. Further, the invention provides functional compost obtained by the above production method, as well as compost for proliferating a filamentous fungus in a bacterial-activity-restricted state.

15 Claims, 6 Drawing Sheets

METHOD FOR PRODUCING FUNCTIONAL COMPOST, FUNCTIONAL COMPOST AND COMPOST FOR PROLIFERATION OF FILAMENTOUS FUNGUS

TECHNICAL FIELD

The present invention relates to: a method for producing a functional compost; a functional compost; and a compost for proliferating a filamentous fungus.

BACKGROUND ART

It is known that filamentous fungi, namely molds, have various functions, which have been beneficially utilized in various fields.

For example, some filamentous fungi have a function to control plant diseases caused by pathogenic filamentous fungi. Pathogenic filamentous fungi may cause diseases, such as damping off, root rot, leaf rot, and wilt in agricultural products including many vegetables, such as cabbage, cucumber, tomato, eggplant and rape leaf, and rice; flowers; trees; turfs, and others. Well-known pathogenic fungi include those belonging to the genus *Rhizoctonia*, the genus *Fusarium*, the genus *Pytium*, the genus *Trichoderma*, and the genus *Sclerotium*. Although chemicals, so-called agricultural chemicals, are generally applied in order to control such plant diseases caused by filamentous fungi, methods of biological control using microorganisms (so called microbial pesticides), which are believed to be safer to the environment, have been proposed and some have been used practically.

Known examples thereof include a technique to utilize bacteria belonging to the genus *Pseudomonas* for controlling a plant disease caused by a filamentous fungus (see e.g. JP 11-187866 A), a technique to utilize a nonpathogenic filamentous fungus belonging to the genus *Trichoderma* or the genus *Mucor* (e.g. see JP 10-150978 A), and a technique to utilize a nonpathogenic filamentous fungus belonging to the genus *Fusarium* (see e.g. WO 97/31521).

Meanwhile, a certain filamentous fungus having a control function against such a pathogenic filamentous fungus has been discovered and a technique to utilize it as a non-residual plant disease control agent having a stable disease control activity has been developed (see e.g. WO 2006/085567). In case such a plant disease control agent is carried by compost, not only a stable plant disease control activity can be obtained, but also a soil improvement effect can be expected.

Further, a decomposing material for chlorinated organic compounds such as a dioxin is known which is obtained by culturing basidiomycetous white-rot fungi, which is another filamentous fungus having a function, on a microbial carrier with a C/N ratio of 30 to 35 (see e.g. JP 2003-334061 A). Further a filamentous fungus belonging to the genus *Trichoderma* is known to have a significant decomposing activity on petroleum related materials, especially on a crude oil and an aromatic hydrocarbon fraction which is a persistent component of the crude oil (see e.g. JP 06-319529 A).

However, even if such a filamentous fungus having a function is carried in compost having a soil improvement activity, it takes long time before the intended filamentous fungus stabilizes in the carrier compost. Furthermore, since bacteria also participate in composting, simple addition of a specific filamentous fungus during a composting process may not lead to efficient proliferation, or successful development, of the intended function.

DISCLOSURE OF THE INVENTION

Means for Solving the Problems

The present invention has been made in view of the above circumstances and provides: a method for producing a functional compost; a functional compost; and a compost for proliferating a filamentous fungus.

According to a first aspect of the present invention, a method for producing a functional compost is provided, the method including: inoculating a compost with a filamentous fungus having a function, the compost being in a bacterial-activity-restricted state; and cultivating the filamentous fungus in the compost to allow selective proliferation thereof.

According to a second aspect of the present invention, a method for producing a functional compost is provided, the method including: inoculating a compost with a filamentous fungus having a function, the compost including bacteria which are active under growth conditions of a filamentous fungus and able to grow in coexistence with a filamentous fungus, and being in a bacterial-activity-restricted state; and cultivating the filamentous fungus in the compost to allow selective proliferation thereof together with the bacteria able to grow in coexistence with a filamentous fungus.

According to a third aspect of the present invention, a functional compost is provided that is obtained by the above method of production and includes a filamentous fungus having a function.

According to a fourth aspect of the present invention, a compost for proliferating a filamentous fungus is provided, the compost being in a bacterial-activity-restricted state.

According to a fifth aspect of the present invention, a compost for proliferating a filamentous fungus is provided, the compost including bacteria which are active under growth conditions of a filamentous fungus and able to grow in coexistence with a filamentous fungus, and being in a bacterial-activity-restricted state for other bacteria.

The bacterial-activity-restricted state according to the present invention may be exemplified by at least one state selected from the group consisting of the following (1) to (3):

(1) a pH-restricted state in a range of pH 4 to 7;

(2) a water content-restricted state in a range of 20% to 40%; and (3) a nutrient-restricted state, in which the $CO_2$ evolution rate after reaching a maximum $CO_2$ evolution rate is from $1\times10^{-5}$ mol/h/g-dry compost to $3\times10^{-5}$ mol/h/g-dry compost.

BEST MODE FOR CARRYING OUT THE INVENTION

Figure 1:
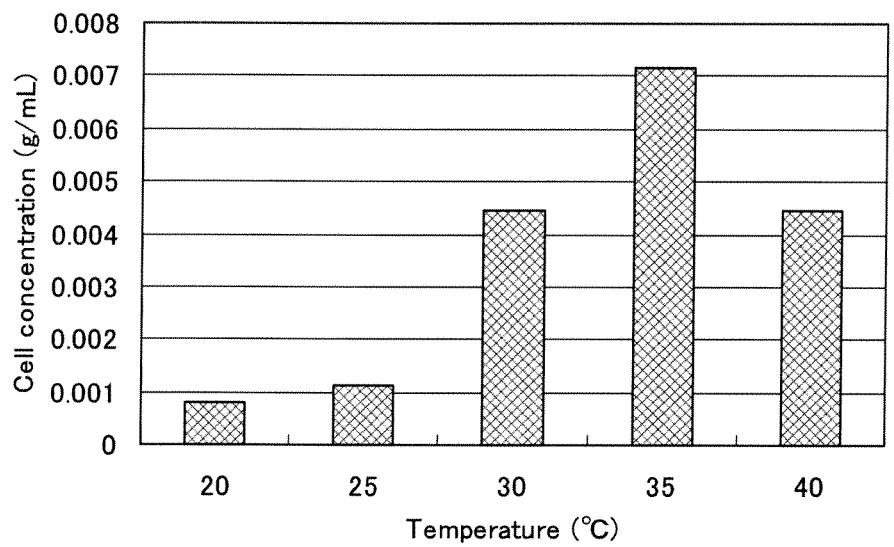
FIG. 1 is a graph showing the optimal temperature for the GM-21 strain according to Example 1 of the present invention.

The method for producing a functional compost in the first aspect of the present invention includes: inoculating a compost with a filamentous fungus having a function, and being in a bacterial-activity-restricted state (inoculation step); and cultivating the filamentous fungus in the compost to allow selective proliferation thereof (proliferation step).

Further, the method for producing a functional compost in the second aspect of the present invention includes: inoculating a compost with a filamentous fungus having a function, the compost including bacteria which are active under growth conditions of a filamentous fungus and able to grow in coexistence with a filamentous fungus, and being in a bacterial-activity-restricted state (inoculation step); and cultivating the filamentous fungus in the compost to allow selective proliferation thereof together with the bacteria able to grow in coexistence with a filamentous fungus (proliferation step).

According to the present invention, since a filamentous fungus and bacteria have different growth environments, a filamentous fungus having a function can be proliferated in compost selectively and more efficiently than bacteria by inoculating and cultivating the filamentous fungus in compost in a bacterial-activity-restricted state. As a result, the proliferated filamentous fungus can be stably established in the compost and a functional compost can be produced efficiently. Consequently, a functional compost stably exerting the intended function can be produced efficiently, and compost effective for such a purpose can be provided.

In the second aspect of the present invention in particular, since a filamentous fungus having a function is inoculated and cultivated in compost that includes bacteria able to grow in coexistence with a filamentous fungus, the bacterial activity of bacteria other than the bacteria able to grow in coexistence with a filamentous fungus is restricted and the bacteria able to grow in coexistence with a filamentous fungus and the filamentous fungus having a function can be selectively and efficiently proliferated. Since the filamentous fungus having a function and the bacteria able to grow in coexistence with a filamentous fungus cooperate to establish and maintain an environment in the functional compost through joint proliferation of the filamentous fungus and the bacteria able to grow in coexistence with a filamentous fungus, an environment favorable to the filamentous fungus having a function can be stably established in the functional compost. As a result, a functional compost can be produced yet more efficiently and a functional compost with a further stabilized intended function can be provided.

The present invention will be described in more detail below. In the present specification, ranges indicated with "to" mean ranges including the numerical values before and after "to" as the minimum and maximum values. Further, the term "step" herein includes not only an independent step, but also a step which may not be clearly separated from another step, insofar as an intended function of the step can be attained.

There is no particular restriction on the filamentous fungus with a function to be used according to the present invention, insofar as a certain function may be expected with the filamentous fungus. Examples thereof include a filamentous fungus with a plant disease control function and a filamentous fungus with a soil improving function that may decompose and decontaminate trichloroethylene, organic solvents, dioxin, PCB, petroleum, hydrocarbons, explosives, agricultural chemicals, biodegradable plastics, and the like. Among them, the filamentous fungus with a plant disease control function, which may make more efficient use of the fertilizing effect of compost, is preferred.

There is no particular restriction on the filamentous fungus with a plant disease control function, insofar as it has a plant disease control function. Examples thereof include inky cap mushrooms (genus *Coprinus*, and genus *Psathyrella*), the genus *Trichoderma*, the genus *Mucor*, the genus *Fusarium*, the genus *Heteroconium*, the genus *Acaulospora*, and the like. Although the filamentous fungus with a plant disease control function can be appropriately selected in accordance with the type of the plant disease, against which a control activity is expected, inky cap mushrooms (genus *Coprinus*, and genus *Psathyrella*) are preferable from the viewpoints of their stable plant disease control functions and broad spectra of effectively applicable plant disease control.

The inky cap mushroom [Hitoyo-take] belongs to the family Coprinaceae, and, from the viewpoint of safety, it preferably belongs to the genus *Coprinus* or the genus *Psathyrella*, that are not the genus *Panaeolus* that is a so-called poisonous mushroom. Among them, *Coprinus curtus, Coprinus cinereus, Coprinus disseminatus, Coprinus comatus, Coprinus atramentarius, Coprinus radians, Psathyrella multissima, Psathyrella candolleana*, and *Psathyrella velutina* are preferably, and these may be used singly or in combinations thereof. Among these, an isolated strain GM-21 (NITE BP-37) belonging to *Coprinus curtus* is particularly preferable, because it is particularly effective in controlling plant diseases.

Examples of the filamentous fungus with a soil improving function include white-rot fungi having a ligninolytic activity. Examples of such white-rot fungi include the genus *Coriolus*, the genus *Phanerochaete* and the genus *Pleurotus*. Furthermore, brown-rot fungi have an activity to decompose aromatic hydrocarbons, and examples of such fungi include the genus *Tyromyces* and the genus *Gloeophyllum*. Examples of other decay fungi include the genus *Trichoderma*. Examples of the filamentous fungus other than these decay fungi include the genus *Fusarium*.

The filamentous fungus to be inoculated into the compost may be a mycelium, a sporophyte or a fruit body of the filamentous fungus, or a crushed substance thereof. Crushing may be carried out with or without drying, and preferably carried out without drying, for example, by stirring with a blade to attain an appropriate size of the crushed substance. When the mycelium is divided in a homogenizer, the fragments of mycelium generally have a diameter of approximately 3 mm at the most, and mostly are of a diameter less than that. The spores of the strain can be used as a fragment having the size as they are. The fruit body of the strain may be, for example, cut into pieces of 1 mm square. Although any size, that is, larger or smaller than that described above, of the fragment is acceptable, reduction in size is favorable for dispersion in or absorption onto something.

The filamentous fungus or a crushed substance thereof may be inoculated into the compost at an amount of, for example, about $8 \times 10^{-6}$ g-dry fungus cells/g-dry compost or more, and preferably, in view of stable growth, about $8 \times 10^{-4}$ g-dry fungus cells/g-dry compost or more, although the amount varies depending on the growth condition of the filamentous fungus.

The term "compost" in the present invention means manure produced by composting an organic waste, and "composting" means a process of degradation treatment of organic substances in an organic waste by the action of microorganisms, to change the state of the organic substances into a state suitable for application to agricultural land. A "composting treatment" generally means storing organic substances under appropriate aeration and stirring conditions for a pre-determined period, to allow fermentation by microorganisms.

The term "compost" as used herein means not only compost in a fully-mature d condition, in which organic substances are completely digested according to the progress of composting, but also compost in an immature condition.

Examples of organic waste to be used for composting include kitchen garbage, sewage sludge and livestock waste; and fish meal, fowl droppings, cattle dung, oil meal, sawdust, wood chips, vegetable debris, fallen leaves, sludge and the like are generally utilized.

Examples of the inoculum to be used for composting include various microorganisms such as bacteria and actinomycetes, and a formulation or a compost product containing these microorganisms may be used directly as an inoculum. Such inoculum used for composting, those commercially available may be used directly.

In the inoculation step, the compost in which bacteria are in a bacterial-activity-restricted state is inoculated with the filamentous fungus having a function. Most bacteria and actinomycetes (also referred to simply as "bacteria" herein) coexisting in the compost and a filamentous fungus having a plant disease control function have different demands on the environment for growth and activity, and therefore an intended filamentous fungus can be selectively proliferated by providing an environment in which bacteria are in a bacterial-activity-restricted state while the filamentous fungus is proliferative and active.

In this case, coexistence of bacteria that are active in the same environment as the filamentous fungus and can coexist with the filamentous fungus (which bacteria are referred to as "bacteria able to grow in coexistence with a filamentous fungus" herein) is preferred. Since the activity of the bacteria able to grow in coexistence with a filamentous fungus is not restricted even in an environment in which the activity of other bacteria participating in composting is restricted, the bacteria can establish a stable bacterial flora together with the filamentous fungus in the compost. Examples of the bacteria able to grow in coexistence with the filamentous fungus include *Virgibacillus halophilus*. An example of *Virgibacillus halophilus* is a *Virgibacillus halophilus* I30-1 strain, which has been deposited with the International Patent Organism Depositary, National Institute of Advanced Industrial Science and Technology, at AIST Tsukuba Central 6, 1-1-1 Higashi, Tsukuba, Ibaraki, Japan, under accession No. FERM ABP-10975 as of 29, May, 2008.

The bacterial-activity-restricted state according to the present invention may be any state in which activities of the bacteria in the compost are restricted and their growth and activities are suppressed, and examples of the state include a state selected from the group consisting of a nutrient-restricted state, a pH-restricted state and a water content-restricted state. The restriction condition may be chosen appropriately singly or in a combination of two or more of such restricted states in accordance with the type(s) of the filamentous fungus and/or bacterium (inoculum) to be utilized, and/or with the environment for producing the compost.

A nutrient-restricted state means a state in which the maturity of a compost has developed and few organic substances remain in the organic waste, such that the compost is in "an almost fully-mature" state. Such an almost fully-mature state can be determined, for example, by a decrease(s) in the C/N ratio and/or the $CO_2$ evolution rate (high level of the conversion of carbon) of the compost and/or transition of the microflora. In such compost in the almost fully-mature state, nutrients are absolutely scarce and activities of bacteria are restricted, but a filamentous fungus may still proliferate in the compost in the nutrient state restricting proliferation of bacteria.

A $CO_2$ evolution rate is defined as a $CO_2$ evolution amount per unit time per unit dry weight of compost, and can be determined easily from measurements of the aeration rate to a compost pile of known weight and the $CO_2$ concentration in the exhaust gas. The $CO_2$ concentration may be measured continuously by a flow cell type infrared absorption CO, meter. Alternatively, the effluent gas may be once collected in a plastic bag such as a Tedlar bag and measured by gas chromatography or a gas detector tube. There in no particular restriction on the amount of the effluent gas to be collected, and for example the amount which can be collected in a 5 L Tedlar bag may be sufficient.

An example of the usable compost in an almost fully-mature state includes a compost whose $CO_2$ evolution rate after reaching a maximum $CO_2$ evolution rate is $1 \times 10^{-5}$ mol/h/g-dry compost to $3 \times 10^{-5}$ mol/h/g-dry compost. The $CO_2$ evolution rate according to the present invention is based on a measurement by using a Kitagawa gas detector tube 126SA or 126SH (Komyo Rikagaku Kogyo K.K.).

A pH-restricted state means a state in which the pH is lower than the optimal pH for bacteria. An example of the pH-restricted state includes pH 4 to 7, and preferably pH 5 to 6.

A water content-restricted state means a state in which the water content is lower than the optimal water content for bacteria. An example of the water content-restricted state includes a state with the water content of 20% to 40% (by mass). The water content may be determined by measuring the compost mass after drying the compost at 105° C. for 48 hours.

A specific bacterial-activity-restricted state can be appropriately selected singly or in combination depending on the growth state of the intended filamentous fungus. By using one of these bacterial-activity-restricted states as a rate-limiting factor, the other conditions can be relaxed, and, from the viewpoint of proliferating more securely and selectively the intended filamentous fungus, at least one selected from the group consisting of the nutrient-restricted state, the pH-restricted state and the water content-restricted state is preferred, and the nutrient-restricted state is still more preferred because it can be realized easily by adjusting the timing of the a filamentous fungus inoculation in the course of composting.

The method for producing the functional compost according to the present invention may be conducted by acquiring compost wherein bacteria are in an bacterial-activity-restricted state (namely, compost for proliferating a filamentous fungus, as described below), or by including further a step of producing such compost.

The step of producing compost means a step to inoculating a composting microorganism in an organic waste and cultivating to degrade organic substances in the organic waste.

In cases where the microorganism is inoculated in an organic waste to be used as a raw material, degradation of organic substances proceeds by cultivation for a pre-determined period to produce compost, and, for efficient composting, it is preferable to set the water content, the pH, or the like at the optimal proliferation levels for bacteria in the compost. Thereby, composting by the bacteria may be accelerated. This accelerated composting by setting the water content, the pH, or the like at the optimal proliferation levels for bacteria is herein called "high speed composting" as appropriate.

As the conditions for high-speed composting, the temperature, the water content and the pH inside the compost are preferably adjusted. Optimal activity conditions vary depending on the types of the bacteria and the organic waste, and conditions suitable for proliferation of common thermophilic bacteria and actinomycetes may be generally acceptable, for example, a temperature around 60° C. (e.g. 50 to 65° C.), a water content of 40% to 60%, and a pH of 8.0 to 8.5. By inoculating an inoculum into an organic waste under such optimal conditions and cultivating it, the compost, which is ready for inoculation of the filamentous fungus, may be produced quickly, for example in about 7 days.

For example, to obtain compost in a nutrient-restricted state, the organic waste may be composted to reach a nutrient-restricted state. Depending on the type and activity status of the bacteria and the number of bacteria, the compost in a nutrient-restricted state (an almost fully-mature compost) can be easily obtained by cultivation for, in general, 5 to 7 days under the above-described optimal conditions for bacteria, so that composting proceeds to the almost fully-mature state. Inoculation of the filamentous fungus may be carried out confirming the nutrient-restricted state by, as described above, the C/N ratio, the $CO_2$ evolution rate, or the like as an indicator(s).

Further, to obtain compost in a pH-restricted state, the compost pH may be adjusted in the course of composting of the organic waste with an appropriate pH adjusting agent. Examples of a usable pH adjusting agent include sulfuric acid, hydrochloric acid, sodium hydroxide, and calcium hydroxide.

The filamentous fungus is inoculated into the compost in bacterial-activity-restricted state, and cultivated, to allow selective proliferation of the filamentous fungus (proliferation step). In the compost wherein bacteria are in a bacterial-activity-restricted state, despite the existence of the bacteria in the compost, the inoculated filamentous fungus proliferates selectively according to a selection pressure against the bacteria.

Here, if bacteria able to grow in coexistence with the filamentous fungus exist in the compost, when the filamentous fungus proliferates selectively, the bacteria able to grow in coexistence with a filamentous fungus can also proliferate selectively. The bacteria able to grow in coexistence with the filamentous fungus proliferate together with the filamentous fungus and do not inhibit development of the functions of the filamentous fungus. Further, since the bacteria able to grow in coexistence with the filamentous fungus establish, by proliferation, a stable microflora together with the filamentous fungus, when the compost is applied to the soil, invasion by native microorganisms in the soil into the compost may be effectively suppressed. For this reason, when the functional compost according to the present invention is used in the soil, the filamentous fungus having a function can survive stably.

The cultivation temperature is preferably selected so that the bacteria-activity-restricted state of the bacteria may be sustained. For example, 10° C. to 35° C. can be chosen, 20° C. to 35° C. is more preferable, and 27° C. to 30° C. is especially preferable. At 35° C. or below, proliferation of bacteria may be effectively suppressed, and at 10° C. or above an appropriate proliferation rate of the filamentous fungus may be maintained. The cultivation may be conducted with aeration, at a pH of 4 to 7, preferably 5 to 6.

The cultivation period may be a duration required for the intended filamentous fungus to proliferate sufficiently in compost, for example 5 days to 7 days. During the cultivation, digestion of organic substances by the filamentous fungus proceeds, and fully-mature compost can be obtained immediately after ending of the cultivation period, when compost in a nutrient-restricted state is used.

In the compost after the completion of the cultivation period, an ample amount of the filamentous fungus is present. For example, in terms of the DNA amount per 1 g of dry compost, about 5 μg/g-dry compost or more, and preferably 30 μg/g-dry compost or more can be obtained.

Since proliferation of the filamentous fungus in the compost may be carried out concurrently with production of the compost according to the producing method of the present invention, functional compost exerting stably its function can be efficiently produced.

Namely, the compost of the present invention obtained according to the producing method of the present invention includes a filamentous fungus having a function. Since the filamentous fungus retains its function and exists at a sufficient amount in the compost, it is functional compost able to exert stably its function. In case the compost includes additionally bacteria able to grow in coexistence with the filamentous fungus, the functional compost may have a more stable function based on the function of the filamentous fungus.

As the bacteria able to grow in coexistence with the filamentous fungus to be included in the functional compost, *Virgibacillus halophilus* is preferable as described above, and specifically the *Virgibacillus halophilus* I30-1 strain may be exemplified.

In case a filamentous fungus having, for example, a plant disease control function is used, the functional compost of the present invention can have various plant disease control functions in accordance with the type of the filamentous fungus having the plant disease control function, and compost having control function against a plant disease whose pathogen is a pathogenic filamentous fungus is preferable, because the control function can be exerted more effectively. Especially in case an inky cap mushroom is selected as the filamentous fungus to be inoculated in the compost, the compost may exert a remarkable plant disease control function, when the pathogenic filamentous fungus belongs to at least one of the genus *Rhizoctonia* and the genus *Fusarium*. As plant diseases, to which a plant disease control agent according to the present invention is applicable, Pak-choi bottom rot, turf leaf rot, melon *Fusarium* wilt, and tomato crown and root rot can be exemplified.

Although the way of use of the functional compost may vary depending on the type of the filamentous fungus in the functional compost and on the purpose, generally an appropriate volume thereof may be mixed into the soil, culture medium or culture soil. For example, for a plant which is the target of the plant disease control, the compost is mixed into the soil, culture medium or culture soil around the root of the plant. Although the mixing ratio varies depending on relative conditions such as the concentration of a pathogen, it is in general preferable to mix compost comprising the filamentous fungus having a plant disease control function into the soil at an appropriate amount, for example, about 1 to 20% by mass, at the fungal cell content of 5 μg/g-dry compost in terms of the DNA amount.

Further, the compost wherein bacteria are in a bacterial-activity-restricted state to be used according to the present invention is the most suitable compost to proliferate a filamentous fungus in the compost including bacteria efficiently for composting, as described above. Namely, the compost for proliferating a filamentous fungus of the present invention is compost in a bacterial-activity-restricted state. Since the compost for proliferating a filamentous fungus of the present invention can cause a filamentous fungus to proliferate efficiently, the above-described functional compost of the present invention can be provided efficiently. Meanwhile, the compost for proliferating a filamentous fungus including bacteria able to grow in coexistence with the filamentous fungus can proliferate the filamentous fungus further efficiently and establish a more stable microflora. As the bacteria able to grow in coexistence with the filamentous fungus to be included in the compost for proliferating the filamentous fungus, *Virgibacillus halophilus* is preferable as described above, and the *Virgibacillus halophilus* I30-1 strain can be exemplified.

The matters described above may be applied without modification to the bacterial-activity-restricted state of the bacteria in the compost for proliferating the filamentous fungus, and the state includes at least one selected from the group consisting of a nutrient-restricted state, a pH-restricted state, and a water content-restricted state. Further, in such a bacterial-activity-restricted state, activities of the bacteria are suppressed and the filamentous fungus may be selectively proliferated.

With respect to the compost for proliferating the filamentous fungus, there is no restriction on the type of the filamentous fungus that can be inoculated as described above, and a filamentous fungus with functions applicable to a broad range of uses can be inoculated and proliferated efficiently.

The present invention can provide a primer set suitable for recognizing and identifying in the functional compost a filamentous fungus having a plant disease control function to be used for producing functional compost. Using the primer set, a sequence specific to the filamentous fungus can be easily amplified by a PCR technique. There is no particular restriction on the PCR technique used herein, insofar as the primer set can be used for amplification.

The primer set, may used to amplify a sequence segment specific to the filamentous fungus in the rDNA of the filamentous fungus. More specifically, to detect the *Coprinus curtus* GM-21 strain, a primer set for the polynucleotide sequence of the ITS1 region, for example GM-21_F and GM-21_R (SEQ ID NOs: 1 and 2) described below can be used. Since the GM-21_F and GM-21_R represented by SEQ ID NOs: 1 and 2 have high specificities to the GM-21 strain, the primer set may be used preferably to detect the GM-21 strain efficiently and accurately, and used especially preferably to detect the GM-21 strain by quantitative PCR.

For example, the primer set can be used as a component of a kit for detecting the GM-21 strain. In other words, the kit for detecting the *Coprinus curtus* GM-21 strain may include a detection primer set of GM-21_F and GM-21_R represented by SEQ ID NOs: 1 and 2 respectively. The kit may include in addition to the primer set, additional components selected from the group consisting of instructions for use required for the detection, reagents to be used for the detection, such as a buffer solution and a reaction solution, and the like, as appropriate. By using the kit, the presence or absence of the GM-21 strain, or the concentration thereof may be determined easily.

Further, the present invention can provide a primer set for detecting and identifying a bacterium able to grow in coexistence with the filamentous fungus. The primer set for detecting the bacterium able to grow in coexistence with the filamentous fungus can be used to amplify a sequence segment specific to the bacterium, in the 16S rDNA. For example, to detect *Virgibacillus halophilus*, a primer set of I30-1_348F (SEQ ID NO: 3) and I30-1_475R (SEQ ID NO: 4), or 16S_F (SEQ ID NO: 5) and 16S_R (SEQ ID NO: 6) can be used. Especially, the primer set of I30-1_348F (SEQ ID NO: 3) and I30-1_475R (SEQ ID NO: 4) has a high specificity to the *Virgibacillus halophilus* I30-1 strain, and the primer set may be preferably used to detect the I30-1 strain efficiently and correctly, and especially preferably used to detect the I30-1 strain by quantitative PCR.

For example, the primer set may be used as a component of a kit for detecting a bacterium able to grow in coexistence with the filamentous fungus. In other words, the kit for detecting the bacterium able to grow in coexistence with the filamentous fungus may include a detection primer set of I30-1_348F and I30-1_475R represented by SEQ ID NOs: 3 and 4 respectively. The kit may include in addition to the primer set, additional components selected from the group consisting of instructions for use required for the detection, reagents to be used for the detection, such as a buffer solution and a reaction solution, and the like, as appropriate. By using the kit, identification of the type of the bacterium able to grow in coexistence with the filamentous fungus or measurement of the concentration thereof may be carried out easily.

The present invention will now be described in more detail by way of Examples below, provided that the present invention should not be construed to be limited thereto.

EXAMPLES

Example 1

Study of Optimal Temperature for GM-21 Strain

The *Coprinus curtus* GM-21 strain (*Coprinus curtus* Kalchbr ex Thum. GM-21: NITE BP-37) grown adequately on PDA medium was cut together with the medium into a 3 mm-square size, which was inoculated into 100 mL of PD liquid medium, and cultured at respective temperatures of 20° C., 25° C., 30° C., 35° C. and 40° C. for 3 days under shaking with a stroke length of 7 cm at 110 spm using a reciprocal shaking culture apparatus (TA-12R, Takasaki Scientific Instruments Corp.). Samples under the respective culture conditions were recovered, and the dry weights of the proliferated GM-21 strain were measured. The results are shown in FIG. 1.

As shown in FIG. 1, the proliferation amount hit a maximum at 35° C., indicating that the proliferation proceeds best around that temperature.

However, the bacteria used for composting proliferate prolifically at 40° C., therefore a preferable temperature condition for obtaining the functional compost efficiently under coexistence of the bacteria was found to be 35° C. or lower. In Example 2 below, the GM-21 strain shake-cultured at 35° C. and 110 spm for 3 days was used.

Example 2

Method for Producing Functional Compost I

To commercially available oil meal compost (Aburakasu (oil meal): Fujimi Engei K.K.) used as a raw material, an inoculum (Aurace G: Matsumoto Institute of Microorganisms Co., Ltd.) was inoculated such that its content becomes 5% based on the dry weight, and the initial pH was set to 8.44, and the water content was set to 59.4%. The temperature was raised from 30° C. to 60° C. over 0 to 12 hours after the inoculation, and the mixture was cultivated at 60° C. to carry out high-speed composting.

During the composting, the $CO_2$ evolution rate was measured by an instrument (Kitagawa gas detector tube 126SA or 126SH: Komyo Rikagaku Kogyo K.K.), and the compost was autoclaved for sterilization (121° C., 90 min) when the $CO_2$ evolution rate decreased to $2 \times 10^{-5}$ mol/h/g-dry compost or less (7 days after the inoculation). At that time, the pH was about 8, which was suitable for the proliferation of the bacteria taking part in high-speed composting, and the water content was 62.3%. The conversion of carbon was as high as 47.4% indicating that the compost at this state was "an almost fully-mature state" (see FIG. 2 and Table 1).

Figure 2:
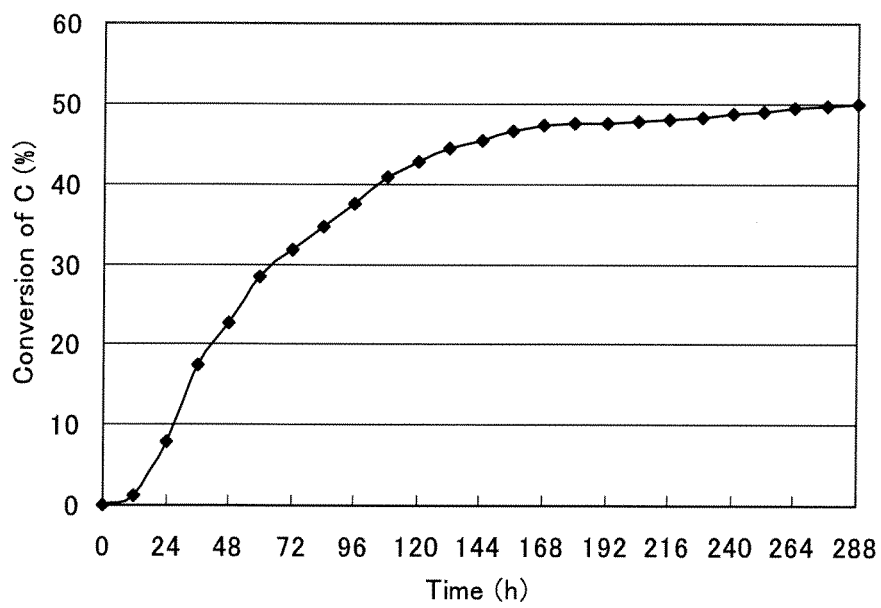
FIG. 2 is a graph showing a time course of the conversion of carbon during a composting process according to Example 2 of the present invention.

After sterilization of the compost in the almost fully-mature state, the pH thereof was adjusted to 5.75 with an aqueous solution of sulfuric acid, and 0.5 mL of the GM-21 strain (0.0076 g-dry fungal cells/mL) was inoculated. The water content was 58.8% at this time. Then composting was carried out at 30° C. for 5 days. At the completion of the cultivation, the pH of the compost was 5.8, the water content was 63.5%, and the conversion of carbon was 50% (FIG. 2 and Table 1).

TABLE 1

| Time (h) | conversion of carbon (%) | pH | Water content (%) | Temperature (° C.) |
|---|---|---|---|---|
| 0 | 0 | 8.44 | 59.4 | 30 |
| 12 | 1.3 | — | — | 60 |
| 24 | 8.0 | — | — | ↓ |
| 36 | 17.5 | — | — | ↓ |
| 48 | 22.6 | — | — | ↓ |
| 60 | 28.3 | — | — | ↓ |
| 72 | 31.7 | — | — | ↓ |
| 84 | 34.7 | — | — | ↓ |
| 96 | 37.6 | — | — | ↓ |
| 108 | 40.8 | — | — | ↓ |
| 120 | 42.8 | — | — | ↓ |
| 132 | 44.4 | — | — | ↓ |
| 144 | 45.5 | — | — | ↓ |
| 156 | 46.6 | — | — | ↓ |
| 168 | 47.4 | 8.12 | 62.3 | ↓ |
| 168 | | | | 30 |
| 180 | 47.5 | 5.75 | 58.8 | ↓ |
| 192 | 47.6 | — | — | ↓ |
| 204 | 47.7 | — | — | ↓ |
| 216 | 48.0 | — | — | ↓ |
| 228 | 48.3 | — | — | ↓ |
| 240 | 48.7 | — | — | ↓ |
| 252 | 49.1 | — | — | ↓ |
| 264 | 49.4 | — | — | ↓ |
| 276 | 49.7 | — | — | ↓ |
| 288 | 50.0 | 5.8 | 63.5 | ↓ |

After the cultivation, the fungal cells were recovered and the fungal cell amount of the GM-21 strain was measured in terms of the DNA amount. To describe simply, the DNA in the compost was extracted using a soil extraction kit (IS OIL for Beads Beating (No. 319-06201): Nippon Gene Co., Ltd.) according to the attached manual. Then the extracted amount of the DNA was measured by usage of Quant-iT (Trade name) PicoGreen dsDNA Reagent and Kits (Invitrogen Corp.) according to the attached manual and measurement of the fluorescence using a fluoro-spectrophotometer, to determine the DNA amount in the compost. Since the compost in an almost fully-mature state had been sterilized, the DNA increased in the compost was believed to be derived from the inoculated GM-21 strain. The fungal cell amount of the GM-21 strain after the composting is shown in Table 2.

As shown in Table 2, a large amount of the GM-21 strain was present in the compost after completion of composting, and the GM-21 strain proliferated about 100-fold in the compost in an almost fully-mature state composted by the bacteria. Since the bacteria in the compost were removed by the sterilization treatment just before the inoculation of the GM-21 strain, they were not present in the obtained functional compost.

TABLE 2

| GM-21 fungal cell amount (μg/g-dry compost) | |
|---|---|
| Immediately after inoculation | Five days later |
| 0.31 | 49.73 |

Comparative Example

To commercially available oil meal compost (Aburakasu (oil meal): Fujimi Engei K.K.) used as a raw material, 1.0 mL of the GM-21 strain (0.0052 g-dry fungal cells/mL) was inoculated, and the initial pH was set to 6, and the water content was set to about 60%. The mixture was cultivated at 35° C. for 5 days after the inoculation. After 5 days was the compost recovered, and proliferation of the GM-21 was examined on PDA medium using a dilution plate technique, to confirm clearly that the filamentous fungus did not proliferate sufficiently in the cultivated compost.

As mentioned above, a filamentous fungus having a plant disease control function cannot proliferate exclusively and selectively, even if the filamentous fungus is inoculated into commercially available compost and cultivated under conditions suitable for proliferation, e.g. at the optimal temperature, because activities of bacteria are not restricted in the compost. Therefore, it can be seen that an adequate and stable function cannot be expected from the yielded compost.

Example 3

The plant disease control activity of the functional compost obtained in Example 2 was examined.

As a pathogen of Pak-choi bottom rot disease, the *Rhizoctonia solani* Pak-choi 2 strain was inoculated in PD liquid medium, shake-cultured at 25° C. and 110 spm (reciprocal shaking) for 7 days, and the resulting product was homogenized to prepare a pathogenic fungal suspension. Then, 47 g of potting soil was placed in an autoclavable plant test pot (AGC Techno Glass Co., Ltd.) and autoclaved for sterilization, and 3 g of the functional compost obtained in Example 2 was mixed therewith. Then the above-described pathogenic fungal suspension and sterilized water were combined to attain a total volume of 12 mL, and the resulting suspension was added to the above mixture of the soil and the compost such that the concentration of the inoculated Pak-choi 2 strain becomes 0.000528 g-dry fungal cells/g-dry soil. The resulting mixture was mixed well, and 15 sterilized seeds of Pak-choi were seeded thereto. The pot was placed in a plant growth chamber (Shimadzu Rika Corp.) and cultivation was carried out at 30° C. by day and 20° C. by night and at a humidity of 55%. Six days after the seeding, seedlings of Pak-choi were thinned to 10, and thereafter the disease progression was observed for 20 days.

The disease progression was measured as a disease severity. The disease severity was quantified as follows:

Disease severity (%)=(1a+2b+3c+4d+5e)×100/(5× seed number)

a: Number of individuals slightly infected
b: Number of individuals infected
c: Number of individuals significantly infected
d: Number of individuals withered
e: Number of individuals not geminated or withered to death In a test plot A were used the functional compost of Example 2 and the pathogenic fungus, in a test plot B was used only the pathogenic fungus, and in a test plot C was not inoculated the pathogenic fungus. The results are shown in FIG. 3, wherein an open circle represents the test plot A, a square represents the test plot B, and a rhombus represents the test plot C.

Figure 3:
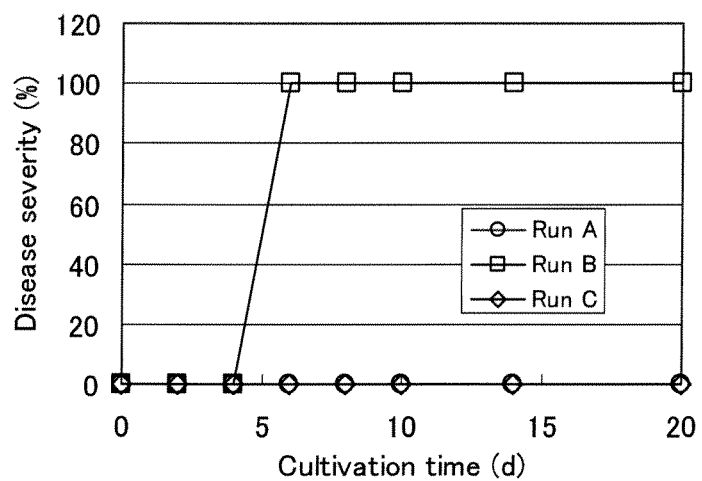
FIG. 3 is a graph demonstrating the control activity of the functional compost against a Pak-choi bottom rot disease according to Example 3 of the present invention.

As obvious from FIG. 3, the functional compost yielded in Example 2 (open circle) exerted a significant control activity against onset of the disease.

Example 4

Method for Producing Functional Compost II

As a raw material, commercially available oil meal compost (Aburakasu (oil meal): Fujimi Engei K.K.) was used. After adjusting the initial pH to 7.86, and the water content to 60%, the oil meal compost was inoculated with an inoculum (Aurace G: Matsumoto Institute of Microorganisms Co., Ltd.) to attain a dry weight ratio of 19:1, and 15 g of the obtained compost raw material mixture was charged into each mini-reactor, which was then subjected to composting.

The temperature was raised from 30° C. to 60° C. over 0 to 12 hours, and high-speed composting was carried out at 60° C. up to 192 hours. Eight days (192 hours) later, a part of the compost was autoclaved for sterilization at 121° C. for 90 min.

The sterilized compost and the unsterilized compost were mixed appropriately to attain the bacterial concentrations of $10^6$ CFU/g-dry compost and $10^3$ CFU/g-dry compost, and the pH of the respective samples were artificially adjusted to about 6 using 10% by volume sulfuric acid. Then, 1 mL of the GM-21 strain, which had been shaking-cultured in advance using PD liquid medium at 35° C. and 110 rpm for 3 days (0.0068 g-dry fungal cells/mL), was inoculated to each sample, to attain the final concentration of 0.00113 g-dry fungal cells/g-dry compost.

The respective samples, whose bacterial concentrations were changed to $10^6$ CFU/g-dry compost and $10^3$ CFU/g-dry compost and to which the GM-21 strain was inoculated, were composted by cultivation at 30° C. for 5 days to obtain the functional compost samples 1 and 2. Both of the functional compost samples 1 and 2 include bacteria able to grow cohabiting with the GM-21 strain, which bacteria have already been included in the compost before the innoculation of the GM-21 strain.

Example 5

Evaluation of Compost

After the completion of composting, the bacterial concentrations of the respective samples 1 and 2 were measured by a dilution plate technique (TS medium, 30° C.). Further, the concentration of the GM-21 strain in the compost, in which the bacteria were present at a high concentration, was measured by quantitative PCR. Further, the $CO_2$ concentration was measured using a Kitagawa gas detector tube as in Example 2, and the plant disease control activity of the compost was evaluated by conducting a test on a plant. Blending of the compost was not carried out for 5 days.

The timing of the inoculation of the GM-21 strain was decided based on the $CO_2$ evolution rate during composting. In this Example, the inoculation was conducted when the $CO_2$ evolution rate reached about $2\times10^{-5}$ mol/h/g-dry compost.

The results are shown in FIGS. 4 through 7.

Figure 4:
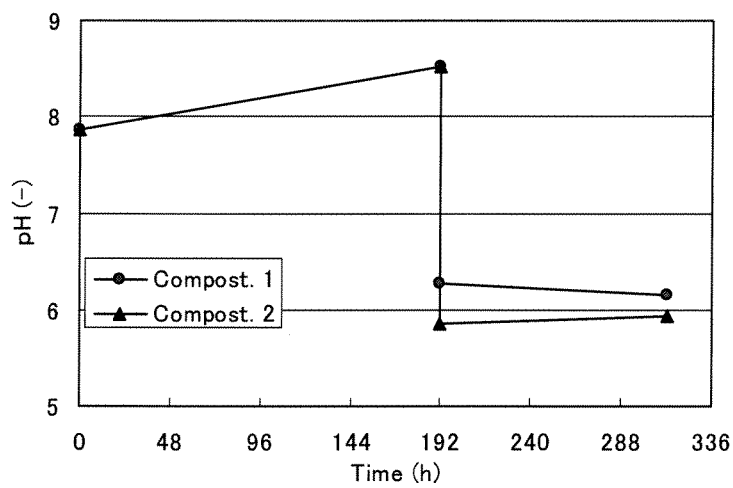
FIG. 4 is a graph showing the pH change during the composting process according to Example 5 of the present invention.

As shown in FIG. 4, the pH values of the functional compost samples 1 and 2 increased from 8 to 8.5 in the course of high-speed composting, indicating the smooth progress of composting. The pH values of the respective compost samples were lowered to about 6 when the inoculations of the GM-21 strain were conducted, and, since organic substances had been digested adequately by the high-speed composting, the pH values did not rise again, providing favorable conditions for proliferation of the GM-21 strain.

Figure 5:
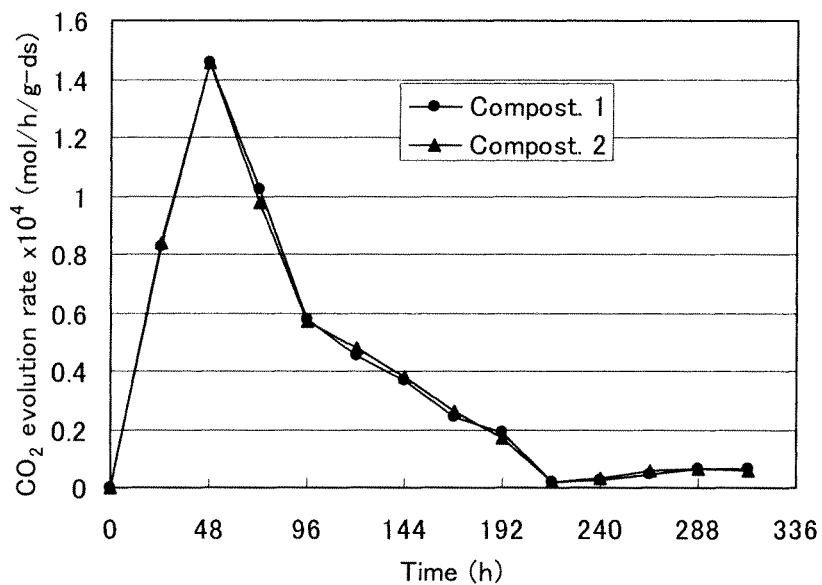
FIG. 5 is a graph showing a time course of the carbon dioxide evolution rate during the composting process according to Example 5 of the present invention.

FIG. 5 shows the time course of the $CO_2$ evolution rate during composting. As shown in FIG. 5, the $CO_2$ evolution rate after the inoculation of the GM-21 strain was low, the result indicating that the residual amount of organic substances at the time of the inoculation of the GM-21 strain is limited, and that the GM-21 strain can proliferate even under a low nutrient condition.

Figure 6:
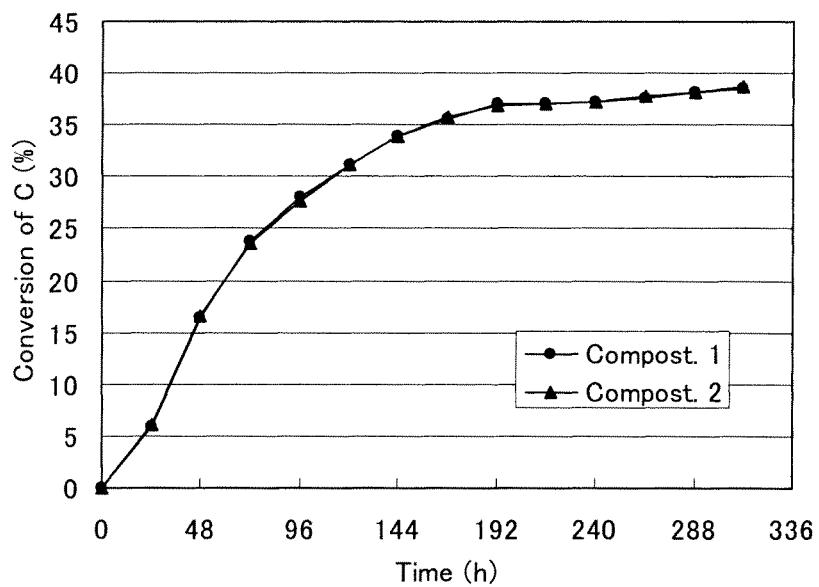
FIG. 6 is a graph showing a time course of the conversion of carbon during the composting process according to Example 5 of the present invention.

FIG. 6 shows the time course of the conversion of carbon during composting. The final conversion of carbons were as high as about 40%, indicating that organic substances in the raw materials were digested adequately.

Figure 7:
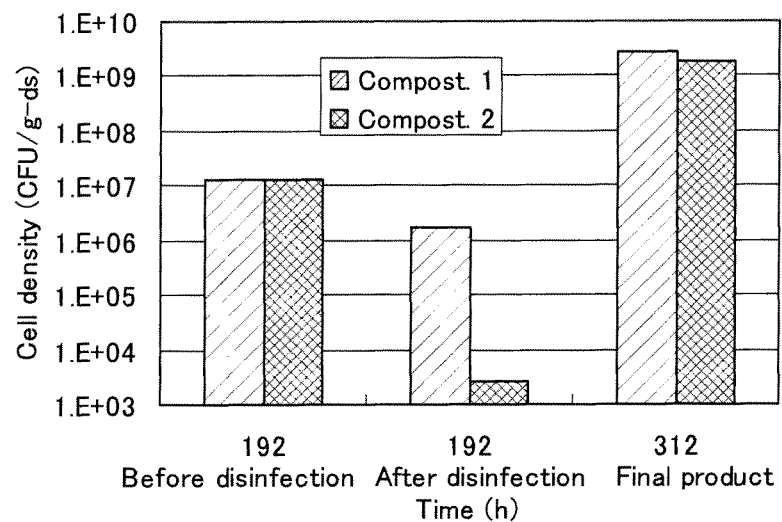
FIG. 7 is a graph showing a time course of the concentration of bacteria in compost during the composting process according to Example 6 of the present invention.

FIG. 7 shows the time course of the bacterial concentrations during composting. The bacterial concentration at the inoculation of the GM-21 strain was about $10^6$ CFU/g-dry compost in the case of the functional compost sample 1, and $10^3$ CFU/g-dry compost in the case of the functional compost sample 2, and the concentration was as high as $10^9$ CFU/g-dry compost or higher at the completion of composting for both the functional compost sample 1 and sample 2. Meanwhile, it was confirmed separately that the types of the bacteria were different before and after the composting, namely the proliferated bacteria were different from those predominant at the inoculation of the GM-21 strain.

(Determination of Concentration of GM-21 Strain in Compost)

The concentrations of the GM-21 strain in the producing process of the functional compost samples 1 and 2 were measured by a quantitative PCR technique. The quantitative PCR was carried out using a real time PCR apparatus: Smart Cycler II (Takara Bio Inc.); a Taq polymerase for amplifying DNA: SYBR Premix Ex Taq (Takara Bio Inc.); and primers:

```
forward primer (GM-21_F):
                                    (SEQ ID NO: 1)
GTGTTGCATGTAGCTGCCTCCTC,
and reverse primer (GM-21_R):
                                    (SEQ ID NO: 2)
TGACGCGAGAGTTATCCAGACCTAC.
```

Figure 8:
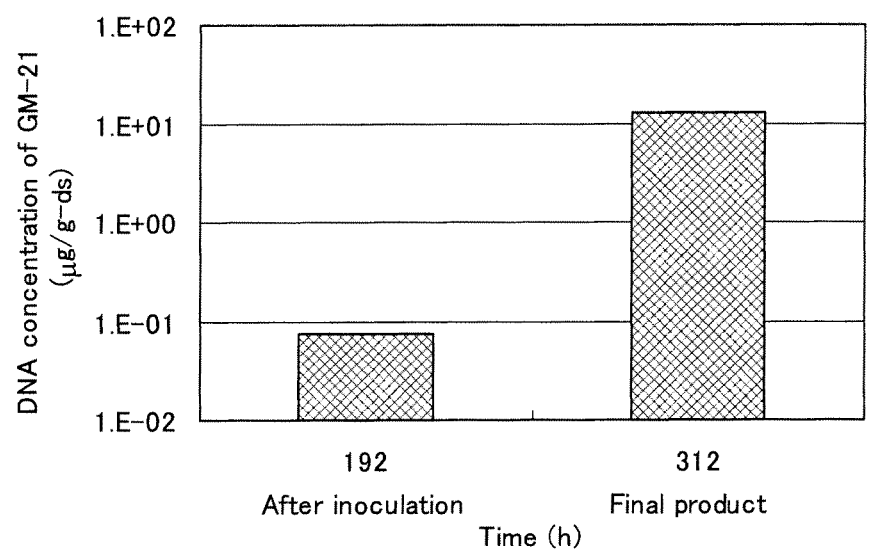
FIG. 8 is a graph showing a time course of the concentration of the GM-21 strain in compost during the composting process according to Example 6 of the present invention.

The PCR reaction condition was: heat denaturation at 95° C. for 10 sec.; followed by 40 cycles of heat denaturation at 95° C. for 5 sec, and annealing and elongation at 60° C. for 20 sec. (see Table 3). The results are shown in FIG. 8.

TABLE 3

| Primer | Forward: GTGTTGCATGTAGCTGCCTCCTC |
| | Reverse: TGACGCGAGAGTTATCCAGACCTAC |

| PCR reaction conditions | | | |
| --- | --- | --- | --- |
| | Number of cycles | Temperature (° C.) | Time (s) | Fluorescence measurement |
| Initial denaturation | — | 95 | 10 | off |
| Denaturation | 40 | 95 | 5 | off |
| Annealing and elongation | | 60 | 20 | on |
| Melting curve analysis | — | 60→95 | 0.2° C./s | off |

FIG. 8 shows the time course of the concentration of the GM-21 strain during composting. As shown in FIG. 8, in the case of the functional compost sample 2, the GM-21 strain proliferated, since the time of the inoculation of the GM-21 strain, not less than 100-fold by the end of the cultivation. As obvious from the above, in the functional compost sample of the present Example, the bacteria able to grow in coexistence with the filamentous fungus were coexistent during the high-speed composting step, and, even in cases where the GM-21 strain was inoculated into the sample in the presence of the bacteria able to grow in coexistence with the filamentous fungus, the GM-21 strain could still proliferate. Furthermore, it was made clear that the GM-21 strain can proliferate irrespective of the amount of the bacteria able to grow in coexistence with the filamentous fungus.

Further, in the present Example, some samples were sterilized before inoculation of the GM-21 strain, but inoculation of the GM-21 strain into samples after high-speed composting, which samples have not been sterilized at all, also caused similar proliferation of the GM-21 strain.

The above has led to the understanding that, in cases where the bacteria able to grow in coexistence with the filamentous fungus are present at the time of the inoculation of the GM-21 strain, the bacteria able to grow in coexistence with the filamentous fungus and the GM-21 strain proliferate together.

Example 6

Identification of Bacteria Able to Grow in Coexistence with Filamentous Fungus

Bacteria in the functional compost sample 1 obtained in Example 4 at the end of composting (bacteria concentration: $10^9$ (—FU/g-dry compost) were cultured by a dilution plate technique using Trypticase soy (hereinafter abbreviated as "TS") medium at 30° C. Three days later, from the plate was isolated a predominant bacterium, which was defined as the I30-1 strain.

By a culture on TS agar medium at 30° C. for 2 days, the I30-1 strain forms a colony having a color of light yellow, a circular form with a diameter of 2 mm, a convex elevation, an entire margin, a smooth surface and a butyrous consistency. The I30-1 strain is a Gram-positive, motile spore-forming bacillus, and catalase- and oxidase-positive.

The bacterium was cultured using TS liquid medium at 30° C. and 110 spm (reciprocal shaking) for 72 hours, and the bacterial cells were recovered by centrifugation at 15,000 rpm for 10 min. DNA was extracted from the recovered bacterial cells using an ISOIL for Beads Beating kit (Nippon Gene Co.). The extracted DNA was purified using Microspin S-300 HR Columns (GE Healthcare UK Ltd.) according to the accompanied manual.

The 16S rDNA region of the extracted and purified saprophytic bacterium was amplified by PCR by a PTC-100 thermal cycler (TaKaRa Shuzo Co.) using primers of 16S_F (AGAGTTTGATCCTGGCTCAGGA: SEQ ID NO: 5) and 16S_R (GGTTACCTTGTTACG: SEQ ID NO: 6), and TaKaRa Ex Taq Hot Start Version (TaKaRa Bio Inc.). The PCR was conducted with the initial denaturation at 95° C. for 5 min; followed by 30 cycles of denaturation at 95° C. for 1 min, annealing at 49° C. for 45 sec. and elongation at 72° C. for 1 min 30 sec.; and the final elongation at 72° C. for 5 min.

The base sequence of the PCR product was analyzed by an ABI PRISM 310 Genetic Analyzer (Applied Biosystems). Then the determined base sequence was subjected to a homology search (nucleotide BLAST) against sequences deposited in the DNA Data Bank of Japan (hereinafter abbreviated as "DDBJ") to find a sequence with the highest homology. As a result, the I30-1 strain was identified as *Virgibacillus halophilus* (see Table 4). The result of the BLAST search on the I30-1 strain is shown in Table 5.

The I30-1 strain was subjected to quantitative PCR using I30-1_348F (GTAGGGAATC TTCCGCAATG: SEQ ID NO: 3) and I30-1475R (GTCAAGGTGC CGCCTTATT: SEQ ID NO: 4) as primers for detection, under conditions similar to those for detection of the above-mentioned GM-21 strain. To be concise, the PCR was conducted using a real time PCR apparatus Smart Cycler II (Takara Bio Inc.) with the initial heat denaturation at 95° C. for 10 sec.; followed by 40 cycles of heat denaturation at 95° C. for 5 sec., and annealing and elongation at 60° C. for 20 sec. Thereby the I30-1 strain was detected quantitatively at high accuracy.

TABLE 4

| AAGCTGGCGG | CGTGCCTAAT | ACATGCAAGT | CGAGCGCGGG | AAGCAGGATG | ATCCTCATCT | 60 |
| GAGGTGATTC | CTGTGGAACG | AGCGGCGGAC | GGGTGAGTAA | CACGTGGGCA | ACCTGCCTGT | 120 |
| AAGATCGGGA | TAACTCGTGG | AAACGCGAGC | TAATACCGGA | TGATACTTTT | CATCGCATGG | 180 |
| TGAGAAGTTG | AAAGATGGCT | TTAAGCTATC | ACTTACAGAT | GGGCCCGCGG | CGCATTAGCT | 240 |
| AGTTGGTGGG | GTAACGGCCT | ACCAAGGCAA | CGATGCGTAG | CCGACCTGAG | AGGGTGATCG | 300 |
| GCCACACTGG | GACTGAGACA | CGGCCCAGAC | TCCTACGGGA | GGCAGCAGTA | GGGAATCTTC | 360 |
| CGCAATGGAC | GAAAGTCTGA | CGGAGCAACG | CCGCGTGAGT | GATGAAGGTT | TTCGGATCGT | 420 |

TABLE 4-continued

```
AAAACTCTGT TGTCAGGGAA GAACAAGTGC CGTTTGAATA AGGCGGCACC TTGACGGTAC    480

CTGACCAGAA AGCCCCGGCT AACTACGTGC CAGCAGCCGC GGTAATACGT AGGGGGCAAG    540

CGTTGTCCGG AATTATTGGG CGTAAAGCGC GCGCAGGCGG TCTTTTAAGT CTGATGTGAA    600

AGCCCACGGC TTAACCGTGG AGGGTCATTG GAAACTGGAG GACTTGAGTG CAGAAGAGGA    660

GAGTGGAATT CCATGTGTAG CGGTGAAATG CGTAGAGATA TGGAGGAACA CCAGTGGCGA    720

AGGCGACTCT CTGGTCTGCA ACTGACGCTG AGGCGCGAAA GCGTGGGTAG CGAACAGGAT    780

TAGATACCCT GGTAGTCCAC GCCGTAAACG ATGAGTGCTA GGTGTTAGGG GGTTTCCGCC    840

CCTTAGTGCT GAAGTTAACG CATTAAGCAC TCCGCCTGGG GAGTACGGCC GCAAGGCTGA    900

AACTCAAAAG AATTGACGGG GGCCCGCACA AGCGGTGGAG CATGTGGTTT AATTCGAAGC    960

AACGCGAAGA ACCTTACCAG GTCTTGACAT CCTCTGACAG CCTTAGAGAT AAGGTGTTCC   1020

CTTCGGGGAC AGAGTGACAG GTGGTGCATG GTTGTCGTCA GCTCGTGTCG TGAGA        1075
```

TABLE 5

| Homology | Deposited sequences found |
| --- | --- |
| 1071/1073 | dbj\|AB243853.1\|*Virgibacillus halophilus* rrs gene for 16S rRNA, partial sequence |
| 1033/1076 | gb\|AY647304.1\|*Bacillus halodenitrificans* strain MSU1710 16S ribosomal RNA gene, partial sequence |
| 1034/1078 | emb\|AJ009793.1\|BMA9793 *Bacillus marismortui* strain 123, 16S ribosomal RNA |
| 1033/1078 | gb\|AY505533.1\|*Virgibacillus marismortui* strain GSP17 16S ribosomal RNA gene, partial sequence |

Example 7

Plant Disease Control Test

Next, the plant disease control activities of the functional compost sample 1 and the functional compost sample 2 obtained in Example 4 were tested.

Except that the inoculation concentration of the Pak-choi 2 strain was adjusted to 0.029 g-dry fungal cells/pot, 15 sterilized seeds of Pak-choi were seeded in the same manner as in Example 3 to a sterilized soil mixed with the compost to attain a content of 6% by mass, and 6 days after the seeding, the seedlings were thinned to 10. Thereafter, the disease progression was observed and rated as a disease severity. The results are shown in FIG. 9, wherein a closed rhombus represents the test lot D with the functional compost sample 1 obtained in Example 4 and the pathogenic fungus, a closed triangle represents the test lot E with the functional compost sample 2 obtained in Example 4 and the pathogenic fungus, a closed square represents the test lot F with solely the pathogenic fungus, and a closed circle represents the test lot G without inoculation of the pathogenic fungus.

Figure 9:
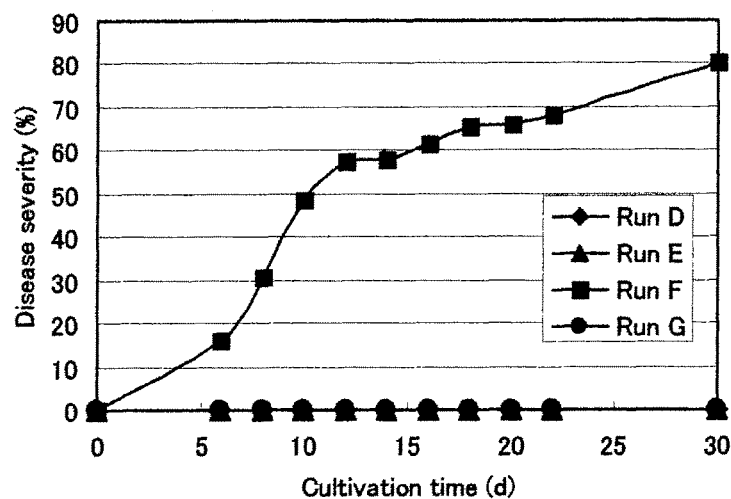
FIG. 9 is a graph demonstrating the control activity of the functional compost according to Example 7 of the present invention against Pak-choi bottom rot disease.

As shown in FIG. 9, the functional compost samples 1 and 2 of the present invention produced in Example 4 by inoculating the GM-21 strain in the presence of the bacteria have been found to have an activity to control Pak-choi bottom rot disease. From the above result, it has been confirmed that even in compost, in which bacteria are present and bacteria able to grow in coexistence with a filamentous fungus have proliferated to a high concentration, the GM-21 strain can proliferate concurrently, and that the present product including a high concentration of the GM-21 strain has an assured disease control activity.

Example 8

Next, control activities against other plant diseases, to which the functional compost is applicable, were tested.
(a) Plant Disease Control Activity Against Lettuce Bottom Rot Pathogen Fifty ml of sterile water was added to 2 g of GM-21 hypha obtained in a similar manner to Example 1, and a mixture obtained was homogenized, to give a suspension A3.

Figure 10:
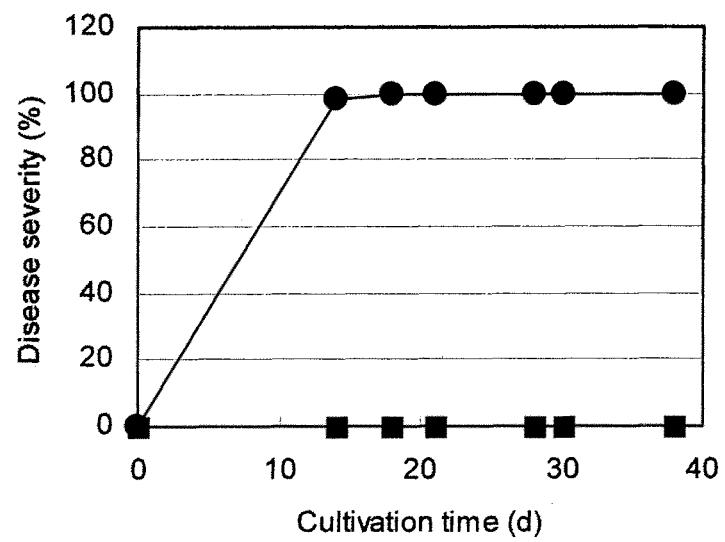
FIG. 10 is a diagram showing the disease progression demonstrating the control activity of the functional compost according to Example 8 of the present invention against lettuce bottom rot disease.

Fifty ml of sterile water was added onto PD agar culture medium having a lettuce bottom rot-causing microbe, *Rhizoctonia solani* lettuce 2, grown thereon; the mixture was homogenized and diluted 1000 fold with sterile water, to give a pathogenic microbe suspension; and the control effect of the *Coprinus curtus* GM-21 suspension A3 on lettuce bottom rot was evaluated. Similarly to Example 1, 2 ml of the pathogenic microbe suspension, 4 ml of the suspensions A3, and 6 ml of sterile water were placed in a sterilized pot containing cultivation soil separately prepared and mixed thoroughly therein; 20 surface sterilized lettuce seeds were added thereto; and the disease development was observed in a plant growth chamber under a condition similar to that in Example 1. Results are summarized in FIG. 10. In FIG. 10, a closed circle represents a test lot using solely the pathogen, and a closed square represents a test lot using the GM-21 strain and the pathogen.

As obvious from FIG. 10, the GM-21 could strongly prohibit a lettuce bottom rot pathogen, *Rhizoctonia solani* lettuce 2 strain, from causing the disease. Consequently, functional compost including the GM-21 strain produced similarly as in Example 2 and Example 4 can have a plant disease control activity also against lettuce bottom rot disease.

(b) Plant Disease Control Activity of Various Filamentous Fungi Belonging to Genus *Coprinus*

Similar to *Coprinus curtus* (GM-21 strain) described above, plant disease control activities of *Coprinus cinereus* (NBRC30114) and *Coprinus disseminatus* (NBRC30972) against turf leaf rot disease by the *Rhizoctonia solani* K1 strain were tested. The results are shown in FIG. 11, wherein a closed circle represents a test plot using solely the pathogen, a closed rhombus represents a test plot using the GM-21 strain and the pathogen, an open triangle represents a test plot using *Coprinus cinereus* and the pathogen, and "X" represents a test plot using *Coprinus disseminatus* and the pathogen, respectively.

Figure 11:
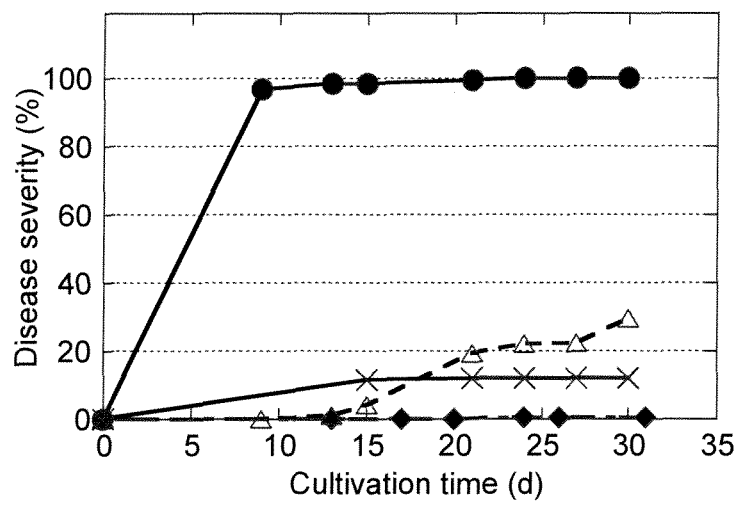
FIG. 11 is a diagram showing the disease progression demonstrating the control activity of the functional compost according to Example 9 of the present invention against turf leaf rot disease.

As obvious from FIG. 11, the *Coprinus curtus* (GM-21 strain), the *Coprinus cinereus* (NBRC30114) and the *Copri-* nus disseminatus (NBRC30972) could control onset of turf leaf rot disease by the *Rhizoctonia solani* K1 strain. Therefore, functional compost including the *Coprinus cinereus* (NBRC30114) or the *Coprinus disseminatus* (NBRC30972), produced similarly as in Example 2 or Example 4 described above using the *Coprinus curtus* GM-21 strain, can have a plant disease control activity against turf leaf rot disease.

(c) Plant Disease Control Activity of Various Filamentous Fungi

A small piece was cut from each of a culture of the *Rhizoctonia solani* Pak-choi 2 on PDA medium and a culture of the GM-21 strain on PDA medium, and placed on a separate PDA medium plate leaving a space of about 5 cm therebetween, which was cultured at 27° C. for 5 days.

Further, each of the *Fusarium oxysporum* f sp. *melonis* F0-Me-2 strain, a pathogen of melon *Fusarium* wilt disease, and the *Fusarium oxysporum* f. sp. *redicus-lycopersici* F0-T-3 strain, a pathogen of tomato crown and root rot disease, was placed similarly as above on a PDA medium plate together with the GM-21 strain, and cultured at 27° C. for 5 days.

As the results, with any of the pathogens, a clear barrage appeared along the interface where the pathogen fungal hypha and the GM-21 strain fungal hypha are facing with each other. Further, the pathogen fungal hypha changed its morphology and color. The above indicates that the pathogen incurred heavy damages by contacting the GM-21 strain.

Consequently, the functional compost including the GM-21 strain produced similarly as in Example 2 or Example 4 can have a plant disease control activity against melon *Fusarium* wilt and tomato crown and root rot disease in addition to lettuce bottom rot disease.

As described above, the plant disease control according to the present invention is not limited to the plant disease control activity of the functional compost including the *Coprinus curtus* GM-21 strain against the pathogen (*Rhizoctonia solani*) of Pak-choi bottom rot disease.

According to an embodiment of the present invention, a step for composting is conducted by selectively proliferating a plant disease-control filamentous fungus, whereby a functional compost having an excellent plant disease control activity can be produced efficiently.

Further, a functional compost produced according to another embodiment of the present invention includes a sufficient amount of a filamentous fungus having a function, whereby the compost can be used to adequately exert an intended function.

Furthermore, a compost according to another embodiment of the present invention, in which bacteria, if any, are in a bacterial-activity-restricted state, is suitable for proliferating a filamentous fungus, and can be used as a compost for proliferating a filamentous fungus.

The disclosure of Japanese Patent Application No. 2007-145697 is hereby incorporated by reference in its entirety.

All the literatures, patent applications and technical standards described in the present specification are hereby incorporated by reference to the same extent as in cases where each literature, patent application or technical standard is concretely and individually described to be incorporated by reference.

The invention claimed is:

1. A functional compost comprising a filamentous fungus having a function and a *Virgibacillus halophilus* bacterium able to grow in coexistence with a filamentous fungus obtained by a method comprising:
    (a) inoculating a compost with a filamentous fungus having a function, the compost comprising a bacterium which is active under growth conditions of a filamentous fungus and able to grow in coexistence with a filamentous fungus, and being in a bacterial-activity-restricted state selected from the group consisting of the following (i) to (iii):
    (i) a pH-restricted state in a range of pH 5 to 7;
    (ii) a water content-restricted state in a range of 20% to 40%; and
    (iii) a nutrient-restricted state, in which the $CO_2$ evolution rate after reaching a maximum $CO_2$ evolution rate is from $1\times10^{-5}$ mol/h/g-dry compost to $3\times10^{-5}$ mol/h/g-dry compost; and
    (b) cultivating the filamentous fungus in the compost to allow selective proliferation thereof together with said-bacterium that is able to grow in coexistence with a filamentous fungus, the method resulting in a functional compost.

2. The functional compost according to claim 1, wherein the filamentous fungus having a function is a filamentous fungus having at least one of a plant disease control function or a soil improvement function.

3. The functional compost according to claim 1, wherein the bacterium able to grow in coexistence with a filamentous fungus is an 130-1 strain, having Accession No. FERM ABP-10975.

4. A method for producing a functional compost, the method comprising:
    inoculating a compost with a filamentous fungus having a function, the compost comprising a *Virgibacillus halophilus* bacterium which is active under growth conditions of a filamentous fungus and able to grow in coexistence with a filamentous fungus, and being in a bacterial-activity-restricted state selected from the group consisting of the following (1) to (3):
    (1) a pH-restricted state in a range of pH 5 to 7;
    (2) a water content-restricted state in a range of 20% to 40%; and
    (3) a nutrient-restricted state, in which the $CO_2$ evolution rate after reaching a maximum $CO_2$ evolution rate is from $1\times10^{-5}$ mol/h/g-dry compost to $3\times10^{-5}$ mol/h/g-dry compost; and
    cultivating the filamentous fungus in the compost to allow selective proliferation thereof together with said bacterium that is able to grow in coexistence with a filamentous fungus, the method resulting in a functional compost.

5. The method according to claim 4, wherein the bacterial-activity-restricted state includes at least said (3) a nutrient-restricted state.

6. The method according to claim 4, further comprising providing a compost in the bacterial-activity-restricted state before the innoculation of a compost with a filamentous fungi having a function.

7. The method according to claim 6, wherein providing the compost to be inoculated with the filamentous fungi having a function comprises composting an organic waste into a nutrient-restricted state.

8. The method according to claim 4, wherein a cultivating temperature for cultivating the filamentous fungus in said compost is 10° C. to 35° C.

9. The method according to claim 4, wherein the bacterium able to grow in coexistence with the filamentous fungus is an 130-1 strain, having Accession No. FERM ABP-10975.

10. The method according to claim 4, wherein the filamentous fungus having a function is a filamentous fungus having at least one of a plant disease control function or a soil improvement function.

11. The method according to claim 10, wherein the filamentous fungus having a plant disease control function is an inky cap mushroom.

12. The method according to claim, wherein the inky cap mushroom is at least one selected from the group consisting of *Coprinus curtus, Coprinus cinereus, Coprinus disseminatus, Coprinus comatus, Coprinus atramentarius, Coprinus radians, Psathyrella multissima, Psathyrella candolliana,* and *Psathyrella velutina.*

13. The method according to claim 12, wherein the inky cap mushroom is the *Coprinus curtus* GM-21 strain (NITE BP-37).

14. The method according to claim 12, the compost having a control function against plant disease caused by a phytopathogenic filamentous fungus.

15. The method according to claim 14, wherein the phytopathogenic filamentous fungus is a filamentous fungus belonging to at least one of the genus *Rhizoctonia* or the genus *Fusarium.*

* * * * *

```
                        SEQUENCE LISTING

<160> NUMBER OF SEQ ID NOS: 7

<210> SEQ ID NO 1
<211> LENGTH: 23
<212> TYPE: DNA
<213> ORGANISM: Artificial
<220> FEATURE:
<223> OTHER INFORMATION: GM-21_F

<400> SEQUENCE: 1
gtgttgcatg tagctgcctc ctc                                            23

<210> SEQ ID NO 2
<211> LENGTH: 25
<212> TYPE: DNA
<213> ORGANISM: Artificial
<220> FEATURE:
<223> OTHER INFORMATION: GM-21_R

<400> SEQUENCE: 2
tgacgcgaga gttatccaga cctac                                          25

<210> SEQ ID NO 3
<211> LENGTH: 20
<212> TYPE: DNA
<213> ORGANISM: Artificial
<220> FEATURE:
<223> OTHER INFORMATION: I30-1_348F

<400> SEQUENCE: 3
gtagggaatc ttccgcaatg                                                20

<210> SEQ ID NO 4
```

```
<211> LENGTH: 19
<212> TYPE: DNA
<213> ORGANISM: Artificial
<220> FEATURE:
<223> OTHER INFORMATION: I30-1_475R

<400> SEQUENCE: 4
gtcaaggtgc cgccttatt                                                  19

<210> SEQ ID NO 5
<211> LENGTH: 22
<212> TYPE: DNA
<213> ORGANISM: Artificial
<220> FEATURE:
<223> OTHER INFORMATION: 16S_F

<400> SEQUENCE: 5
agagtttgat cctggctcag ga                                              22

<210> SEQ ID NO 6
<211> LENGTH: 15
<212> TYPE: DNA
<213> ORGANISM: Artificial
<220> FEATURE:
<223> OTHER INFORMATION: 16S_R

<400> SEQUENCE: 6
ggttaccttg ttacg                                                      15

<210> SEQ ID NO 7
<211> LENGTH: 1075
<212> TYPE: DNA
<213> ORGANISM: Virgibacillus halophilus

<400> SEQUENCE: 7
aagctggcgg cgtgcctaat acatgcaagt cgagcgcggg aagcaggatg atcctcatct      60
gaggtgattc ctgtggaacg agcggcggac gggtgagtaa cacgtgggca acctgcctgt     120
aagatcggga taactcgtgg aaacgcgagc taataccgga tgatactttt catcgcatgg     180
tgagaagttg aaagatggct ttaagctatc acttacagat gggcccgcgg cgcattagct     240
agttggtggg gtaacggcct accaaggcaa cgatgcgtag ccgacctgag agggtgatcg     300
gccacactgg gactgagaca cggcccagac tcctacggga ggcagcagta gggaatcttc     360
cgcaatggac gaaagtctga cggagcaacg ccgcgtgagt gatgaaggtt ttcggatcgt     420
aaaactctgt tgtcagggaa gaacaagtgc cgtttgaata aggcggcacc ttgacggtac     480
ctgaccagaa agcccccggct aactacgtgc cagcagccgc ggtaatacgt aggggggcaag    540 cgttgtccgg aattattggg cgtaaagcgc gcgcaggcgg tctttttaagt ctgatgtgaa    600 agcccacggc ttaaccgtgg agggtcattg gaaactggag gacttgagtg cagaagagga    660
gagtggaatt ccatgtgtag cggtgaaatg cgtagagata tggaggaaca ccagtggcga    720
aggcgactct ctggtctgca actgacgctg aggcgcgaaa gcgtgggtag cgaacaggat    780 tagatacccct ggtagtccac gccgtaaacg atgagtgcta ggtgttaggg ggtttccgcc    840
ccttagtgct gaagttaacg cattaagcac tccgcctggg gagtacggcc gcaaggctga    900
aactcaaaag aattgacggg ggcccgcaca agcggtggag catgtggttt aattcgaagc    960
aacgcgaaga accttaccag gtcttgacat cctctgacag ccttagagat aaggtgttcc   1020
cttcggggac agagtgacag gtggtgcatg gttgtcgtca gctcgtgtcg tgaga        1075
```